US012702271B2

(12) United States Patent
Nagae et al.

(10) Patent No.: US 12,702,271 B2
(45) Date of Patent: Aug. 11, 2026

(54) MEDICAL IMAGING SYSTEM AND IMAGING DEVICE

(71) Applicant: Sony Group Corporation, Tokyo (JP)

(72) Inventors: Satoshi Nagae, Tokyo (JP); Yuichiro Kita, Tokyo (JP)

(73) Assignee: Sony Group Corporation, Tokyo (JP)

( * ) Notice: Subject to any disclaimer, the term of this patent is extended or adjusted under 35 U.S.C. 154(b) by 340 days.

(21) Appl. No.: 18/555,873

(22) PCT Filed: Jan. 31, 2022

(86) PCT No.: PCT/JP2022/003517
§ 371 (c)(1),
(2) Date: Aug. 14, 2024

(87) PCT Pub. No.: WO2022/230270
PCT Pub. Date: Nov. 3, 2022

(65) Prior Publication Data

US 2024/0389834 A1 Nov. 28, 2024

(30) Foreign Application Priority Data

Apr. 27, 2021 (JP) ................................ 2021-075017

(51) Int. Cl.
*G02B 23/24* (2006.01)
*A61B 1/00* (2006.01)

(52) U.S. Cl.
CPC ........ *A61B 1/00096* (2013.01); *G02B 23/243* (2013.01)

(58) Field of Classification Search
CPC ........... A61B 1/00096; A61B 1/00188; A61B 1/00193; A61B 1/00; G02B 23/243; G02B 23/2415; G02B 23/24
(Continued)

(56) References Cited

U.S. PATENT DOCUMENTS 7,075,719 B2 * 7/2006 Osawa .................. H04N 23/55 359/489.08
7,961,244 B2 * 6/2011 Shibazaki ........... G02B 27/288 348/335
(Continued)

FOREIGN PATENT DOCUMENTS

JP 2012-034823 A 2/2012
JP 2017-209154 A 11/2017
(Continued)

OTHER PUBLICATIONS

International Search Report and Written Opinion mailed on Apr. 12, 2022, received for PCT Application PCT/JP2022/003517, filed on Jan. 31, 2022, 9 pages including English Translation.

*Primary Examiner* — Helen Shibru
(74) *Attorney, Agent, or Firm* — XSENSUS LLP

(57) ABSTRACT

The present disclosure relates to a medical imaging system and an imaging device capable of achieving high image quality with a simpler configuration.
An imaging module includes a branching optical system that branches light incident via an imaging lens in three directions and emits the light, and three imaging elements that receive light emitted from the branching optical system in the three directions and perform imaging. Then, the three imaging elements are arranged at positions having different optical distances from the principal point of the imaging lens by a shift amount ΔZ, and the shift amount ΔZ is calculated from ΔZ=2×DoF×M (1<M<2) by using a depth of focus DoF of the imaging lens set on the basis of a pixel pitch p of the imaging elements and an aperture value F of the imaging lens, and a correction term M. The present technology can be applied to, for example, a medical imaging system.

12 Claims, 15 Drawing Sheets

(58) Field of Classification Search
USPC ............................................................ 348/65
See application file for complete search history.

(56) References Cited

U.S. PATENT DOCUMENTS

| | | | | |
|---|---|---|---|---|
| 8,878,919 | B2 * | 11/2014 | Tsuyuki | A61B 1/0005 348/65 |
| 9,030,543 | B2 * | 5/2015 | Tsuyuki | G02B 23/2423 600/109 |
| 9,949,622 | B2 * | 4/2018 | Katakura | G02B 23/04 |
| 11,607,114 | B2 * | 3/2023 | Tsuyuki | A61B 1/051 |
| 11,857,158 | B2 * | 1/2024 | Tsuyuki | G02B 5/04 |
| RE50,292 | E * | 2/2025 | Fukuda | H10F 39/8057 |
| 2002/0114015 | A1 * | 8/2002 | Fujii | H04N 1/2346 348/E5.045 |
| 2019/0142254 | A1 * | 5/2019 | Chiba | A61B 1/000095 600/109 |

FOREIGN PATENT DOCUMENTS

| | | | |
|---|---|---|---|
| WO | 2014/171248 | A1 | 10/2014 |
| WO | 2016/132639 | A1 | 8/2016 |
| WO | 2018/221041 | A1 | 12/2018 |
| WO | 2019/171642 | A1 | 9/2019 |

* cited by examiner

Figure 11:
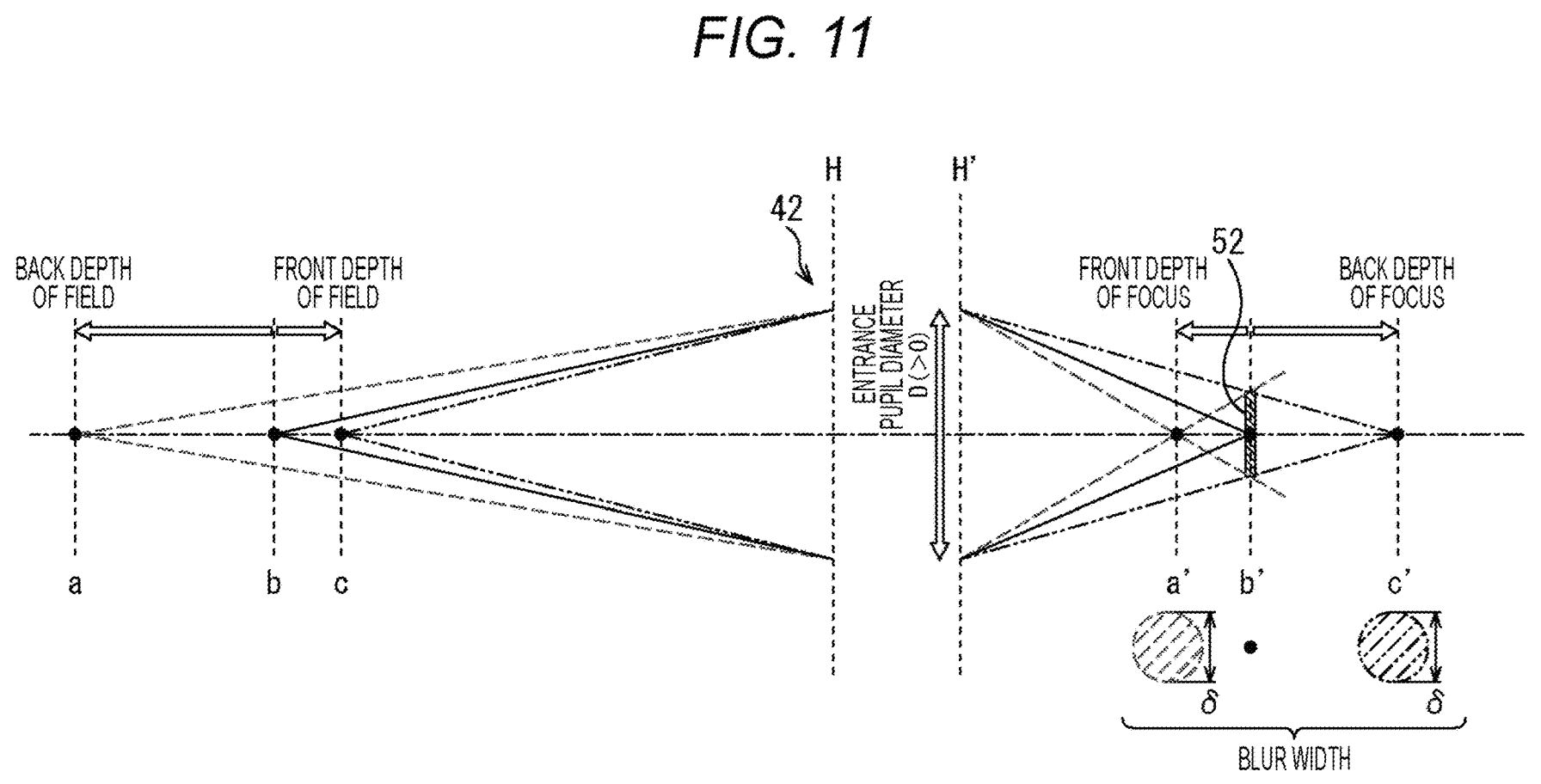

BACK DEPTH OF FOCUS
FRONT DEPTH OF FOCUS
52
c'
b'
a'
$\delta$
$\delta$
BLUR WIDTH
H'
ENTRANCE PUPIL DIAMETER D (>0)
H
42
FRONT DEPTH OF FIELD
BACK DEPTH OF FIELD
c
b
a

MEDICAL IMAGING SYSTEM AND IMAGING DEVICE

TECHNICAL FIELD

The present disclosure relates to a medical imaging system and an imaging device, and more particularly to a medical imaging system and an imaging device capable of achieving high image quality with a simpler configuration.

BACKGROUND ART

In recent years, the resolution of lenses used in medical imaging devices such as endoscopes and surgical microscopes has been increased. Furthermore, in order to increase the resolution of an image captured by the medical imaging device, it is necessary not only to reduce the f-number (aperture value) of the lens but also to reduce the pixel size of the imaging element. However, in a case where the f-number of the lens is reduced or the pixel size of the imaging element is reduced to increase the resolution, an image with a shallow depth of field in which the depth range of a subject that appears to be in focus is narrowed is captured.

For example, in the medical imaging device, by capturing an image having a higher resolution and a deeper depth of field, it is possible to contribute to quick and accurate diagnosis and procedure, and thus it is important to solve the trade-off between the resolution and the depth of field.

Therefore, there has been proposed an endoscope system capable of acquiring a high-quality image with an extended depth of field by using an extended depth of field (EDoF) technology for extending the depth of field (see, for example, Patent Document 1).

CITATION LIST

Patent Document

Patent Document 1: Japanese Patent Application Laid-Open No. 2017-209154

SUMMARY OF THE INVENTION

Problems to be Solved by the Invention

Incidentally, the endoscope system of Patent Document 1 described above is configured to adjust the optical path length difference by relatively sliding two prisms in a direction parallel to abutment surfaces at which the prisms abut. However, in such a configuration, there is a concern that foreign matter is sandwiched between the abutment surfaces in the process of sliding the prisms, and for example, in a lens system having a large f-number such as an endoscope, the foreign matter is likely to appear in an image, and as a result, the image quality is deteriorated.

Furthermore, Patent Document 1 discloses an adjustment range of the prism for performing optical path length difference adjustment from the viewpoint of balance between interference between the prism and a mechanical member and an extension amount for extending the depth of field, but does not disclose any optimum adjustment condition from the viewpoint of image quality for achieving both resolution and the depth of field. Furthermore, an imaging element is bonded to the prism via a cover glass, and has a structure in which the tilt cannot be adjusted. In particular, since two light receiving regions are provided in one imaging element, it is not possible to adjust a difference in tilt between the light receiving regions. For this reason, for example, if there is a tilt, partial blur occurs, and as a result, the resolving power of the lens cannot be sufficiently exhibited.

Moreover, since the endoscope system of Patent Document 1 has a configuration in which two light receiving regions are provided in one imaging element, a prism block needs to include an s- and p-polarized light separation film. Therefore, a $\lambda/4$ plate and a reflection mirror are required in one optical path, and as a result, the cost increases as the number of optical components increases.

Therefore, a technology capable of capturing a high-quality image having a deep depth of field and high resolution with a simpler configuration than that of the endoscope system disclosed in Patent Document 1 is required.

The present disclosure has been made in view of such a situation, and it is an object of the present disclosure to achieve high image quality with a simpler configuration.

Solutions to Problems

A medical imaging system according to one aspect of the present disclosure includes: an imaging module provided in a medical imaging device, the imaging module including a branching optical system that branches light incident via an imaging lens in at least two directions and emits the light, and two or more imaging elements that receive the light emitted from the branching optical system in the at least two directions, respectively, and perform imaging; and an image processing unit that performs image processing of generating an EDoF image with an extended depth of field by using images captured by the two or more imaging elements, the two or more imaging elements are arranged at positions having different optical distances from a principal point of the imaging lens by a shift amount $\Delta Z$, and the shift amount $\Delta Z$ is calculated from $\Delta Z=2\times DoF\times M$ $(1<M<2)$ by using a depth of focus DoF of the imaging lens set on the basis of a pixel pitch p of the two or more imaging elements and an aperture value F of the imaging lens, and a correction term M.

An imaging device according to one aspect of the present disclosure includes: an imaging module including a branching optical system that branches light incident via an imaging lens in at least two directions and emits the light, and two or more imaging elements that receive the light emitted from the branching optical system in the at least two directions, respectively, and perform imaging, the two or more imaging elements are arranged at positions having different optical distances from a principal point of the imaging lens by a shift amount $\Delta Z$, and the shift amount $\Delta Z$ is calculated from $\Delta Z=2\times DoF\times M$ $(1<M<2)$ by using a depth of focus DoF of the imaging lens set on the basis of a pixel pitch p of the two or more imaging elements and an aperture value F of the imaging lens, and a correction term M.

In one aspect of the present disclosure, light incident via the imaging lens is branched in at least two directions by the branching optical system and emitted, and the light emitted from the branching optical system in the at least two directions is received by the two or more imaging elements, respectively, and imaging is performed. Then, the two or more imaging elements are arranged at positions having different optical distances from the principal point of the imaging lens by the shift amount $\Delta Z$, and the shift amount $\Delta Z$ is calculated from $\Delta Z=2\times DoF\times M$ $(1<M<2)$ by using the depth of focus DoF of the imaging lens set on the basis of the pixel pitch p of the two or more imaging elements and the aperture value F of the imaging lens, and the correction term M.

BRIEF DESCRIPTION OF DRAWINGS

FIG. 3 is a view illustrating a first configuration example of an imaging module.

FIG. 11 is a diagram for explaining a blur width on a sensor surface of the imaging element.

FIG. 14 is a view illustrating a second configuration example of the imaging module.

MODE FOR CARRYING OUT THE INVENTION

Hereinafter, a specific embodiment to which the present technology is applied will be described in detail with reference to the drawings.

<Configuration Example of Medical Imaging System>

Figure 1:
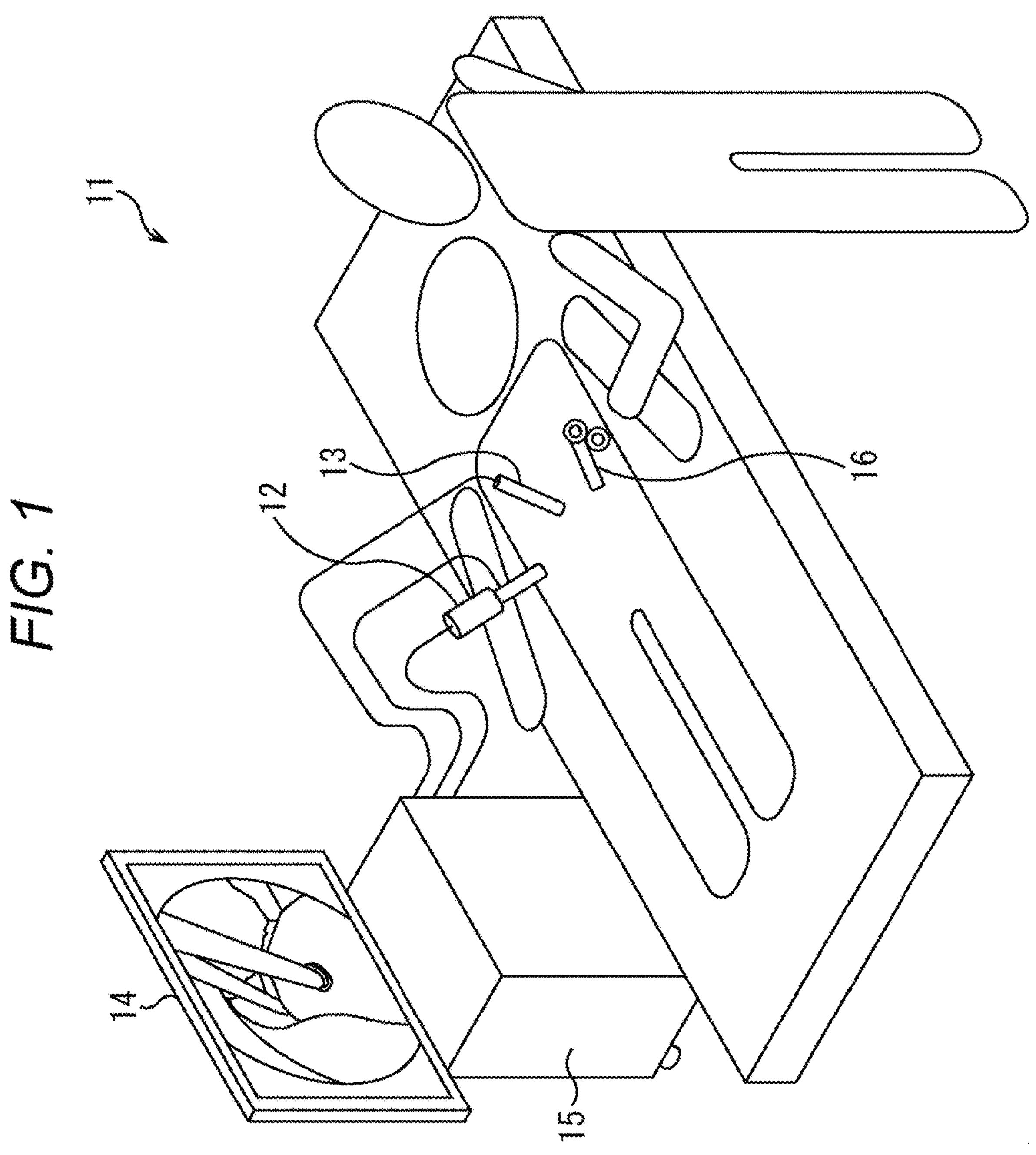
FIG. 1 is a view illustrating a configuration example of an embodiment of a medical imaging system to which the present technology is applied.

FIG. 1 is a view illustrating a configuration example of an embodiment in which a medical imaging system to which the present technology is applied is applied to endoscopic operation.

A medical imaging system 11 illustrated in FIG. 1 includes an endoscope 12, an energy treatment tool 13, a display device 14, and a device unit 15.

For example, in surgery using the medical imaging system 11, the endoscope 12 and the energy treatment tool 13 are inserted into the body of a patient, and forceps 16 are inserted into the body of the patient. Then, in the medical imaging system 11, an image of an affected part such as a tumor imaged by the endoscope 12 is displayed on the display device 14 in real time, and a surgeon can treat the affected part by using the energy treatment tool 13 and the forceps 16 while viewing the image.

Figure 2:
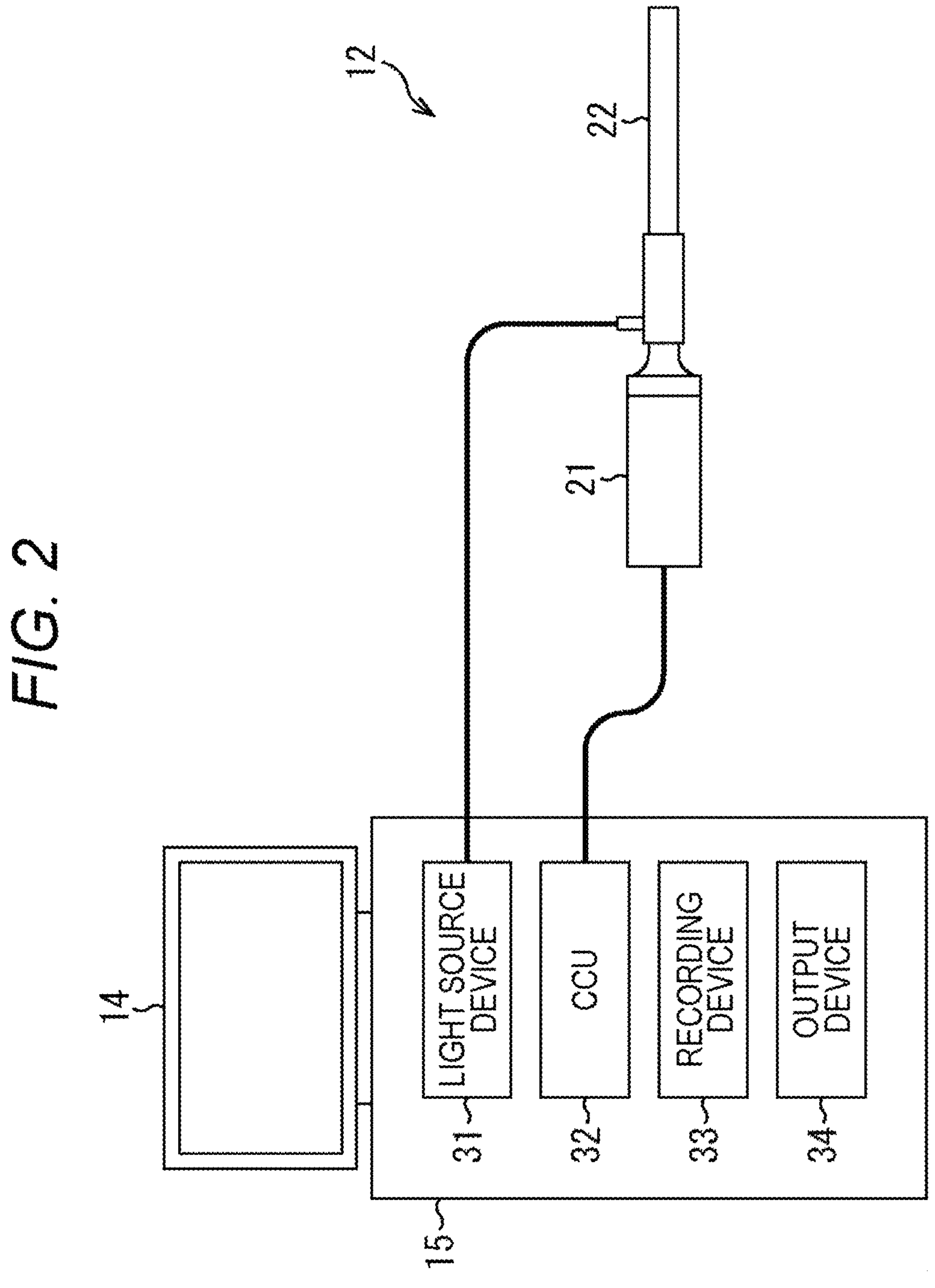
FIG. 2 is a view illustrating a configuration example of an endoscope and a device unit.

For example, as illustrated in FIG. 2, the endoscope 12 is configured such that a cylindrical lens barrel unit 22 in which an optical system such as an objective lens is incorporated is mounted on a camera head 21 in which an imaging module (see FIG. 3) including a plurality of imaging elements and the like is incorporated. For example, the lens barrel unit 22 is a scope formed in a tubular shape using a rigid or flexible material, can guide light to the distal end by a light guide extending inside, and can emit the light into the body cavity of the patient. The camera head 21 can image the inside of the body cavity of the patient via the optical system of the lens barrel unit 22.

The energy treatment tool 13 is, for example, a medical instrument used in endoscopic surgical operation for cutting an affected part or sealing a blood vessel by heat generated by a high-frequency current.

The display device 14 can display an image captured by the endoscope 12 as it is or can display an image subjected to image processing in the device unit 15.

The device unit 15 is configured by incorporating various devices necessary for performing endoscopic operation using the medical imaging system 11. For example, as illustrated in FIG. 2, the device unit 15 can include a light source device 31, a camera control unit (CCU) 32, a recording device 33, and an output device 34.

The light source device 31 supplies light emitted to an affected part when the endoscope 12 performs imaging to the endoscope 12 via an optical fiber or the like.

The CCU 32 controls imaging by the endoscope 12 and performs various types of image processing (for example, image processing of generating an EDoF image as described later) on an image captured by the endoscope 12.

The recording device 33 records the image output from the CCU 32 on a recording medium. The output device 34 prints and outputs the image output from the CCU 32 or outputs the image via a communication network.

<First Configuration Example of Imaging Module>

Figure 3:
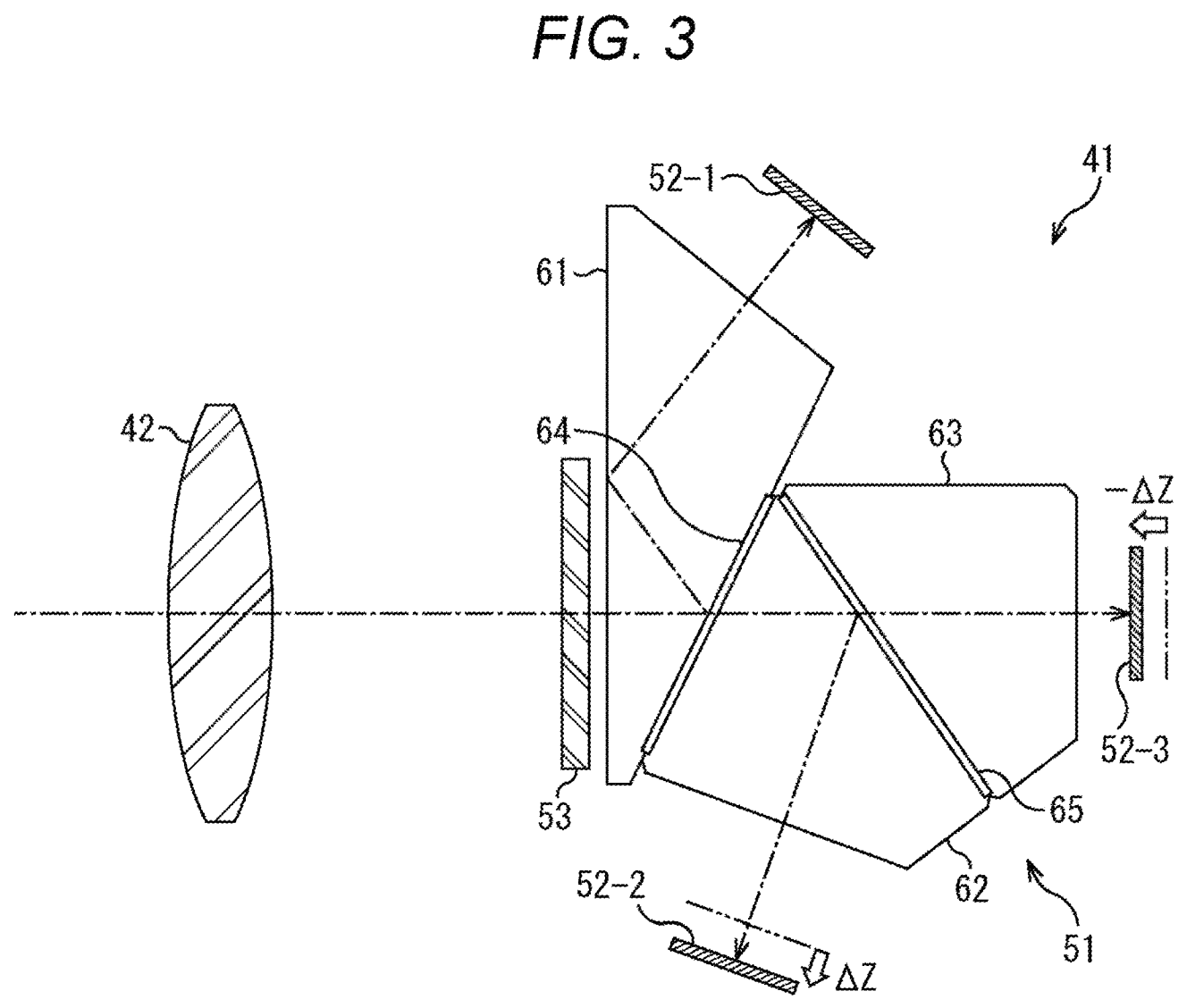

FIG. 3 is a view illustrating a first configuration example of the imaging module incorporated in the camera head 21 of the endoscope 12.

As illustrated in FIG. 3, the imaging module 41 includes a branching optical system 51, three imaging elements 52-1 to 52-3, and an optical element 53. Furthermore, the imaging lens 42 is arranged on an optical axis of light incident on the imaging module 41.

The imaging lens 42 includes one or a plurality of lenses, and condenses light toward the imaging elements 52-1 to 52-3 such that imaging by light entering the lens barrel unit 22 of the endoscope 12 is performed, and causes the light to be incident on the branching optical system 51.

The branching optical system 51 branches the light incident via the imaging lens 42 in three directions toward the imaging elements 52-1 to 52-3. The branching optical system 51 includes a first prism 61, a second prism 62, a third prism 63, a first dichroic mirror 64, and a second dichroic mirror 65.

The first prism 61, the second prism 62, and the third prism 63 constitute a prism block joined so as not to generate an air gap between the first prism 61 and the second prism 62 and between the second prism 62 and the third prism 63. As described above, by adopting the prism block having a so-called gapless structure, in the branching optical system 51, it is possible to avoid occurrence of interposition of process dust, occurrence of exuding of a sealing material, and the like. Therefore, in the branching optical system 51, it is possible to eliminate appearance of foreign matter in an image and suppress deterioration in image quality, for example, even in a lens system having a relatively large f-number like the endoscope 12.

The first dichroic mirror 64 is an optical thin film including a dielectric multilayer film formed on the emission surface of the first prism 61 on the second prism 62 side, and for example, branches light at a light amount at which average reflectance:average transmittance=1:2. Furthermore, the first dichroic mirror 64 branches light in a specific wavelength band including a visible light band from 400 nm to 700 nm, for example.

The second dichroic mirror 65 is an optical thin film including a dielectric multilayer film formed on the emission surface of the second prism 62 on the third prism 63 side, and for example, branches light at a light amount at which average reflectance:average transmittance=1:1. Furthermore, the second dichroic mirror 65 branches light in a specific wavelength band including the visible light band from 400 nm to 700 nm, for example.

The imaging elements 52-1 to 52-3 are, for example, CMOS image sensors having RGB filters in a Bayer array, and each receive light emitted from the branching optical system 51 and perform imaging. The imaging element 52-1 is arranged at a position where an optical distance (optical path length) from the principal point of the imaging lens 42 is an intermediate distance as a reference. The imaging element 52-2 is arranged at a position away from the branching optical system 51 by a shift amount ΔZ such that the optical distance from the principal point of the imaging lens 42 is longer than the reference. The imaging element 52-3 is arranged at a position closer to the branching optical system 51 by the shift amount ΔZ such that the optical distance from the principal point of the imaging lens 42 is shorter than the reference.

Therefore, in a case where the focal length of the imaging lens 42 is adjusted such that the imaging element 52-1 captures an image focused on the region of interest, the imaging element 52-2 captures an image focused on the near point side of the region of interest. Similarly, in this case, the imaging element 52-3 captures an image focused on the far point side of the region of interest. Therefore, hereinafter, an image captured by the imaging element 52-1 will be referred to as a Mid image, an image captured by the imaging element 52-2 will be referred to as a Near image, and an image captured by the imaging element 52-3 will be referred to as a Far image as appropriate. Note that the optical distances of the imaging elements 52-1 to 52-3 from the principal point of the imaging lens 42 may be interchanged. For example, the optical distances may be set such that the imaging element 52-1 can capture a Near image, the imaging element 52-2 can capture a Mid image, and the imaging element 52-3 can capture a Far image.

Therefore, the imaging module 41 is configured to be able to output the Near image, the Mid image, and the Far image to the CCU 32.

As will be described later with reference to FIG. 8, the optical element 53 has a depolarization function of depolarizing light incident on the branching optical system 51 and a color correction function of correcting the color of the light incident on the branching optical system 51.

In the medical imaging system 11 configured as described above, the CCU 32 can generate an EDoF image in which the depth of field is extended more than those of the Near image, the Mid image, and the Far image output from the imaging module 41 by using the Near image, the Mid image, and the Far image, and output the EDoF image to the display device 14. Therefore, the medical imaging system 11 can capture a high-quality image having a deep depth of field and high resolution with a simpler configuration.

<Characteristics of Dichroic Mirror>

Characteristics of the first dichroic mirror 64 and the second dichroic mirror 65 will be described with reference to FIG. 4.

Figure 4:
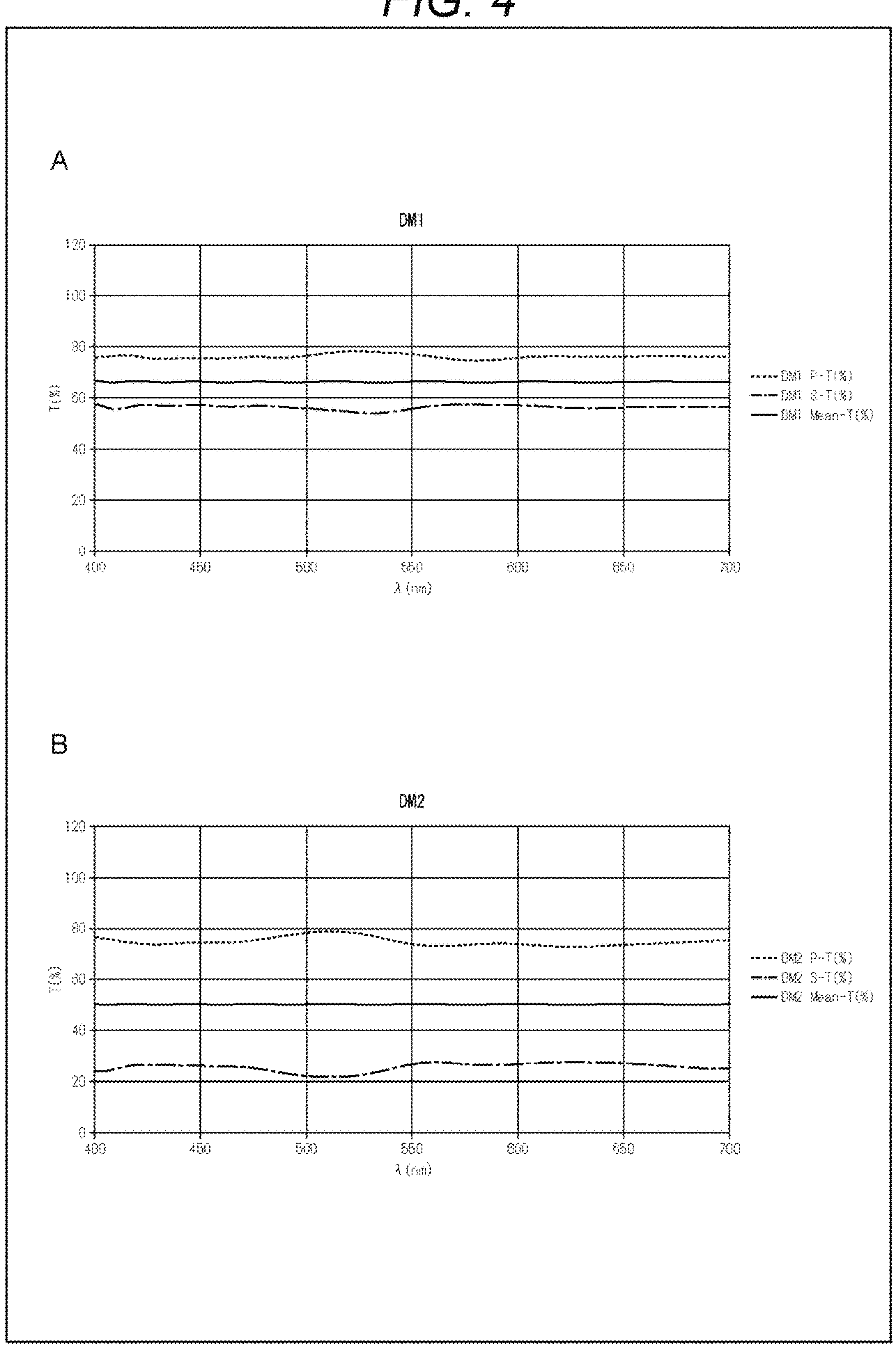
FIG. 4 is a diagram illustrating an example of characteristics of two dichroic mirrors.

A of FIG. 4 illustrates spectral transmittances of p-polarized light, s-polarized light, and the average value of the p-polarized light and the s-polarized light of the first dichroic mirror 64. B of FIG. 4 illustrates spectral transmittances of p-polarized light, s-polarized light, and the average value of the p-polarized light and the s-polarized light of the second dichroic mirror 65.

The first dichroic mirror 64 is configured such that the average value of the p-polarized light and the s-polarized light has a spectral transmittance of about 66%, and the second dichroic mirror 65 is configured such that the average value of the p-polarized light and the s-polarized light has a spectral transmittance of about 50%.

As illustrated, the polarization characteristic difference between the p-polarized light and the s-polarized light in the second dichroic mirror 65 is greater than the polarization characteristic difference between the p-polarized light and the s-polarized light in the first dichroic mirror 64. This is because the branching optical system 51 is configured such that light beam incident angle 35° measured from the normal line of the second dichroic mirror 65 is greater than the light beam incident angle 25.75° measured from the normal line of the first dichroic mirror 64. That is, the branching optical system 51 adopts a gapless prism as described above, and as a result, it is necessary to increase the light beam incident angle on the second dichroic mirror 65 in order to avoid the substrate of the imaging element 52-2 from interfering with the prism block.

Then, in the dielectric multilayer film used for the second dichroic mirror 65, the polarization characteristic difference increases as the light beam incident angle increases, and in the second dichroic mirror 65, the polarization characteristic difference between the p-polarized light and the s-polarized light increases. Note that, in a spectral film including a metal film such as aluminum or chromium, the polarization characteristic difference can be reduced, but there is a concern that light absorption occurs and the light amount decreases. Therefore, it is preferable to use only a dielectric multilayer film for the first dichroic mirror 64 and the second dichroic mirror 65.

<Spectral Characteristics of Imaging Element>

Spectral characteristics of the imaging elements 52-1 to 52-3 calculated according to the characteristics of the first dichroic mirror 64 and the second dichroic mirror 65 as illustrated in FIG. 4 will be described with reference to FIGS. 5 to 7.

In the imaging element 52-1, light reflected by first dichroic mirror 64 and emitted from the first prism 61 forms an image. In the imaging element 52-2, light transmitted through the first dichroic mirror 64, reflected by the second dichroic mirror 65, and emitted from the second prism 62 forms an image. In the imaging element 52-3, light transmitted through the first dichroic mirror 64 and the second dichroic mirror 65, and emitted from the third prism 63 forms an image.

Figure 5:
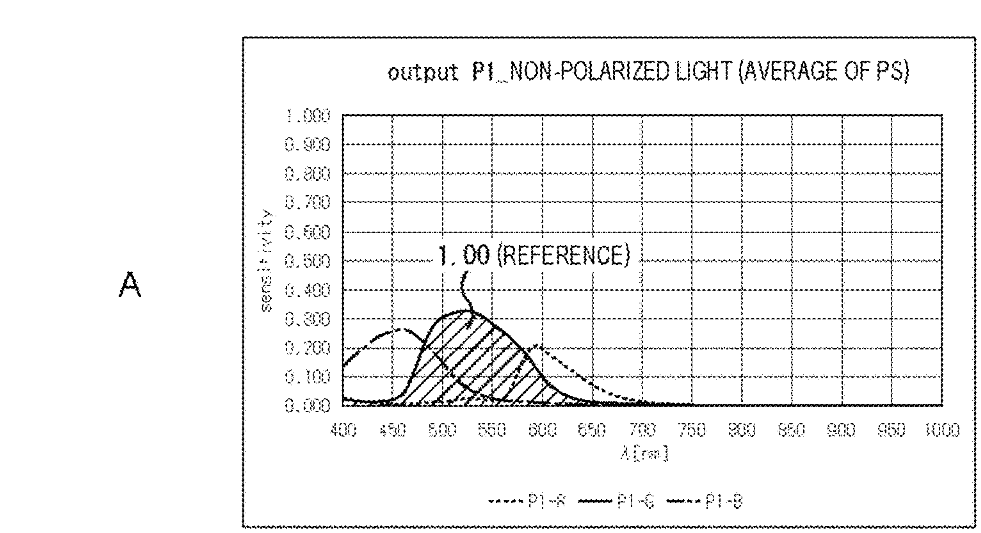
FIG. 5 is a diagram illustrating an example of spectral characteristics of an imaging element in non-polarized light.
Figure 5:
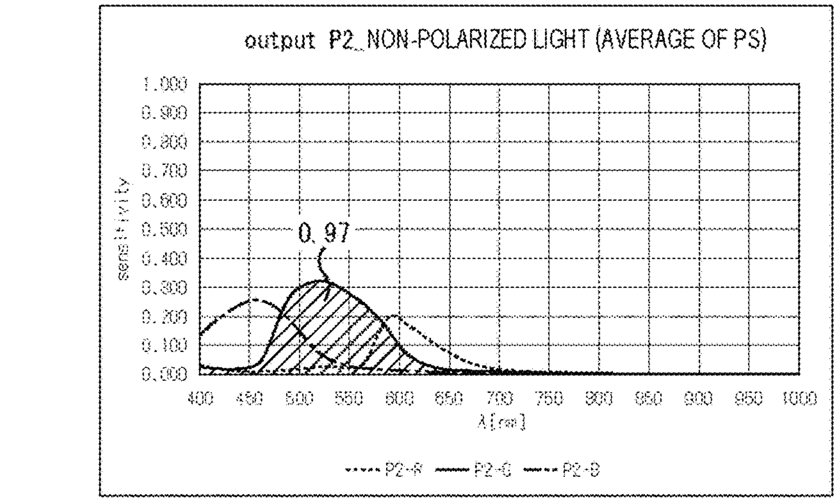
Figure 5:
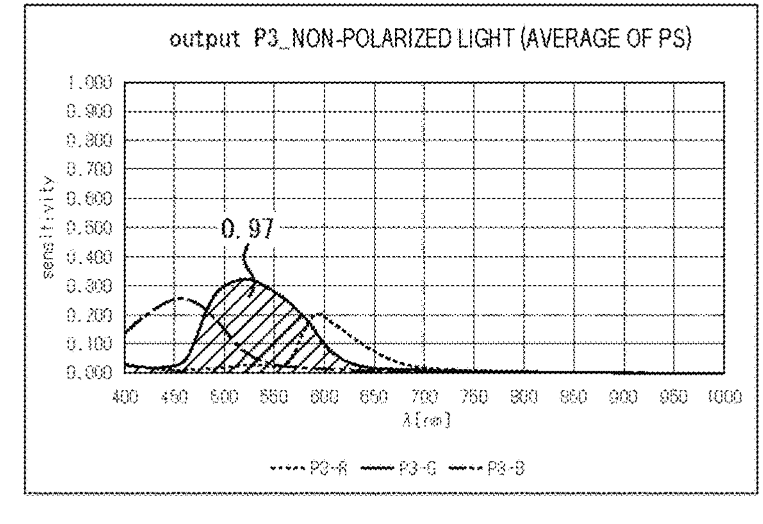

A of FIG. 5 illustrates spectral characteristics of the imaging element 52-1 in non-polarized light (average value of p-polarized light and s-polarized light), B of FIG. 5 illustrates spectral characteristics of the imaging element 52-2 in non-polarized light, and C of FIG. 5 illustrates spectral characteristics of the imaging element 52-3 in non-polarized light. As illustrated, when the area of the green spectrum of the imaging element 52-1 is normalized to 1.00, the area of the green spectrum of the imaging element 52-2 is 0.97, and the area of the green spectrum of the imaging element 52-3 is 0.97.

Figure 6:
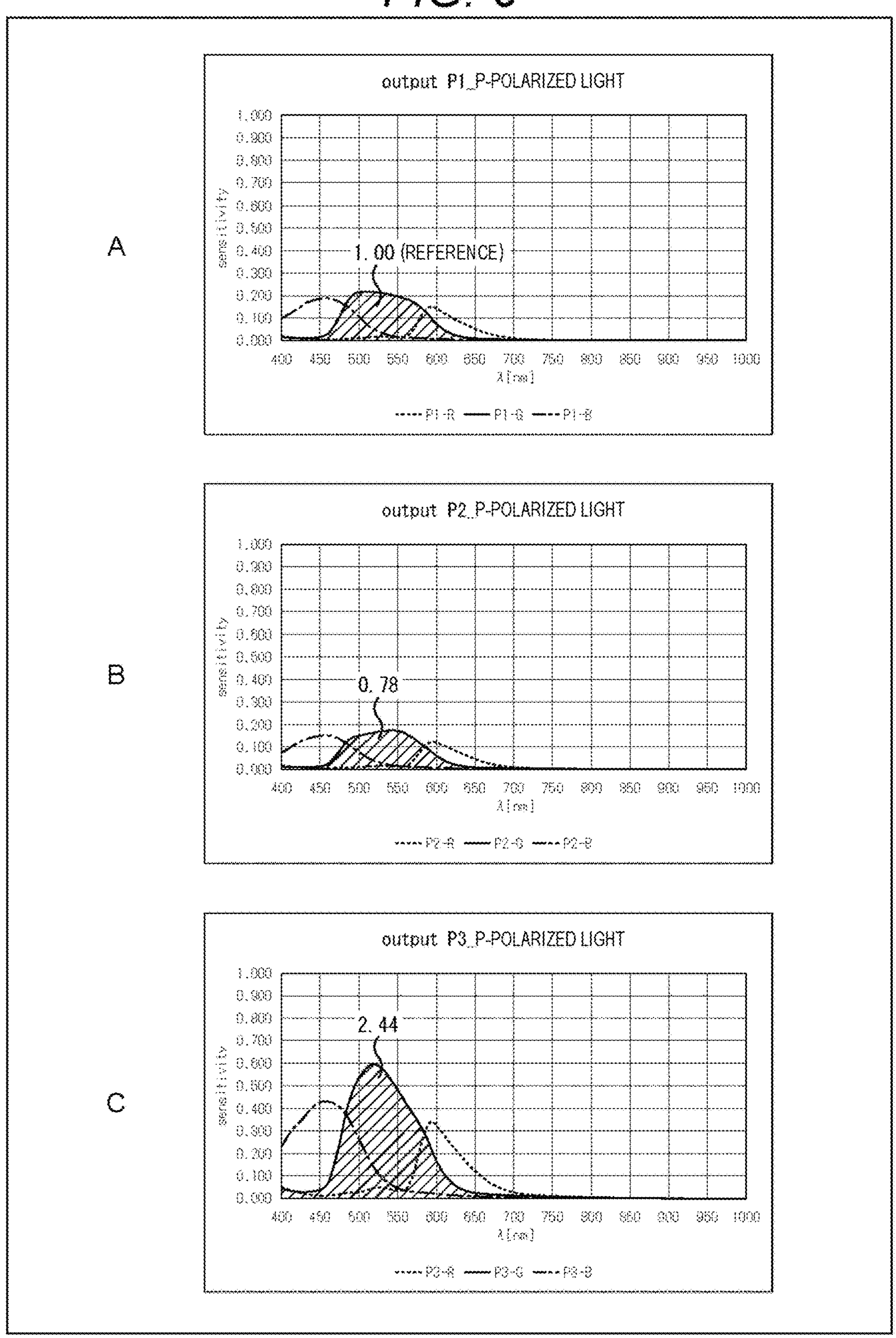
FIG. 6 is a diagram illustrating an example of spectral characteristics of the imaging element in p-polarized light.

A of FIG. 6 illustrates spectral characteristics of the imaging element 52-1 in p-polarized light, B of FIG. 6 illustrates spectral characteristics of the imaging element 52-2 in p-polarized light, and C of FIG. 6 illustrates spectral characteristics of the imaging element 52-3 in p-polarized light. As illustrated, when the area of the green spectrum of the imaging element 52-1 is normalized to 1.00, the area of the green spectrum of the imaging element 52-2 is 0.78, and the area of the green spectrum of the imaging element 52-3 is 2.44.

Figure 7:
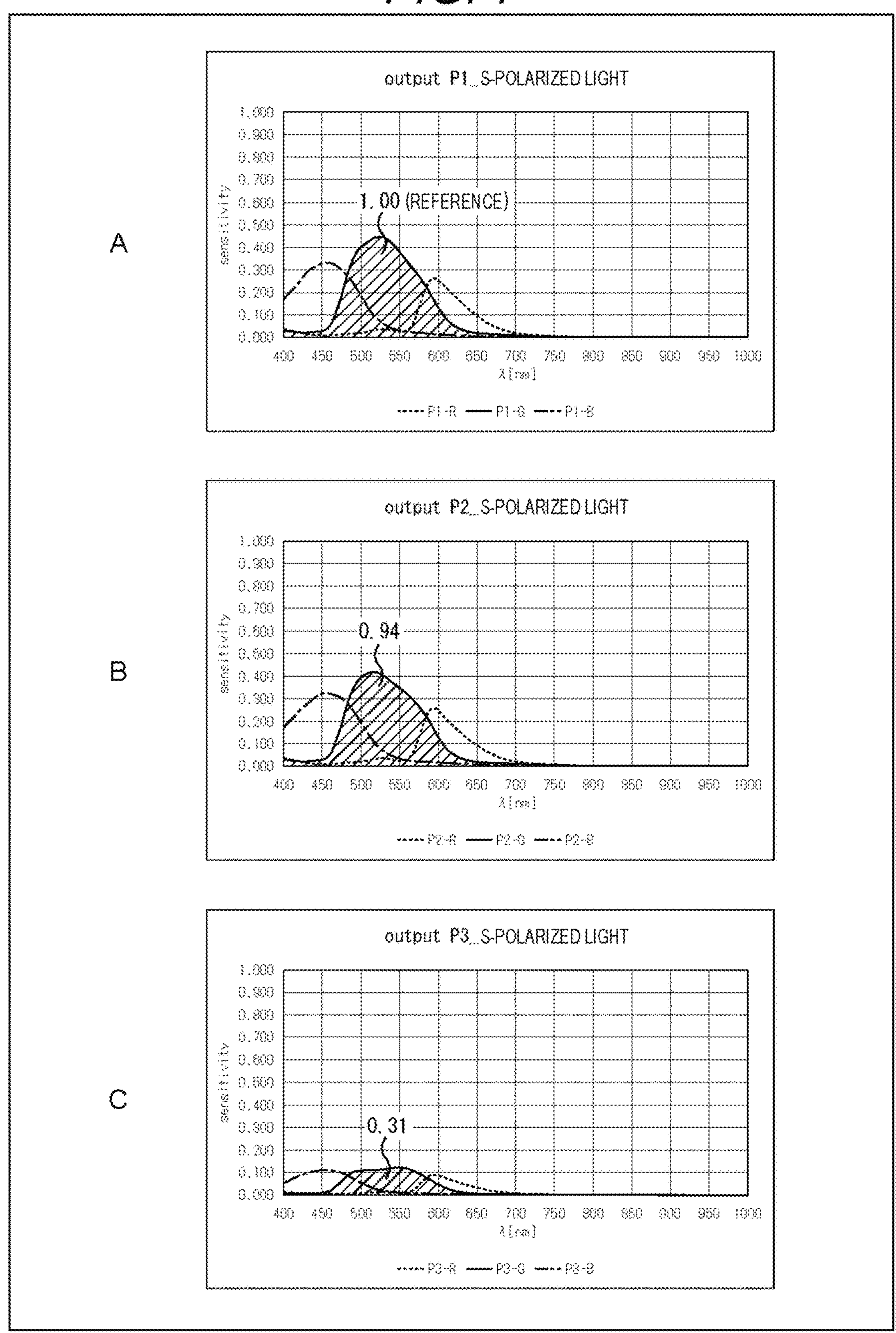
FIG. 7 is a diagram illustrating an example of spectral characteristics of the imaging element in s-polarized light.

A of FIG. 7 illustrates spectral characteristics of the imaging element 52-1 in s-polarized light, B of FIG. 7 illustrates spectral characteristics of the imaging element 52-2 in s-polarized light, and C of FIG. 7 illustrates spectral characteristics of the imaging element 52-3 in s-polarized light. As illustrated, when the area of the green spectrum of the imaging element 52-1 is normalized to 1.00, the area of the green spectrum of the imaging element 52-2 is 0.94, and the area of the green spectrum of the imaging element 52-3 is 0.31.

For example, it may be considered that the area of the green spectrum roughly represents the degree of exposure, and as illustrated in FIGS. 5 to 7, the exposure of the imaging element 52-3 greatly changes depending on the polarization state of the subject. That is, with respect to the exposure (1.00) of the imaging element 52-1, in the case of the p-polarized light, the exposure (2.44) of the imaging element 52-3 increases, and in the case of the s-polarized light, the exposure (0.31) of the imaging element 52-3 decreases, which appears as differences in exposure.

<Configuration Example of Optical Element>

A configuration example of the optical element 53 will be described with reference to FIGS. 8 and 9.

For example, in endoscopic surgery, it is considered that reflection from a metallic treatment tool such as forceps or reflected light from a glossy organ is often p-polarized or s-polarized. Therefore, there is a concern that the polarization characteristic difference of the second dichroic mirror 65 appears as a difference in exposure of the imaging element 52-3 with respect to the imaging element 52-1, and as a result, the image quality of the EDoF image is deteriorated.

Therefore, the medical imaging system 11 can avoid the degradation of the image quality of the EDoF image due to the polarization characteristic difference of the second dichroic mirror 65 by eliminating the p-polarized light or the s-polarized light of the light incident on the branching optical system 51 by the depolarization function of the optical element 53. Moreover, the optical element 53 needs to have a color correction function (for example, infrared ray cutting) for bringing the spectral characteristics of the imaging elements 52-1 to 52-3 close to the visibility curve together with such a depolarization function. That is, the medical imaging system 11 is configured such that the optical element 53 having the depolarization function and the color correction function is arranged in a limited space, that is, the front surface of the branching optical system 51.

Figure 8:
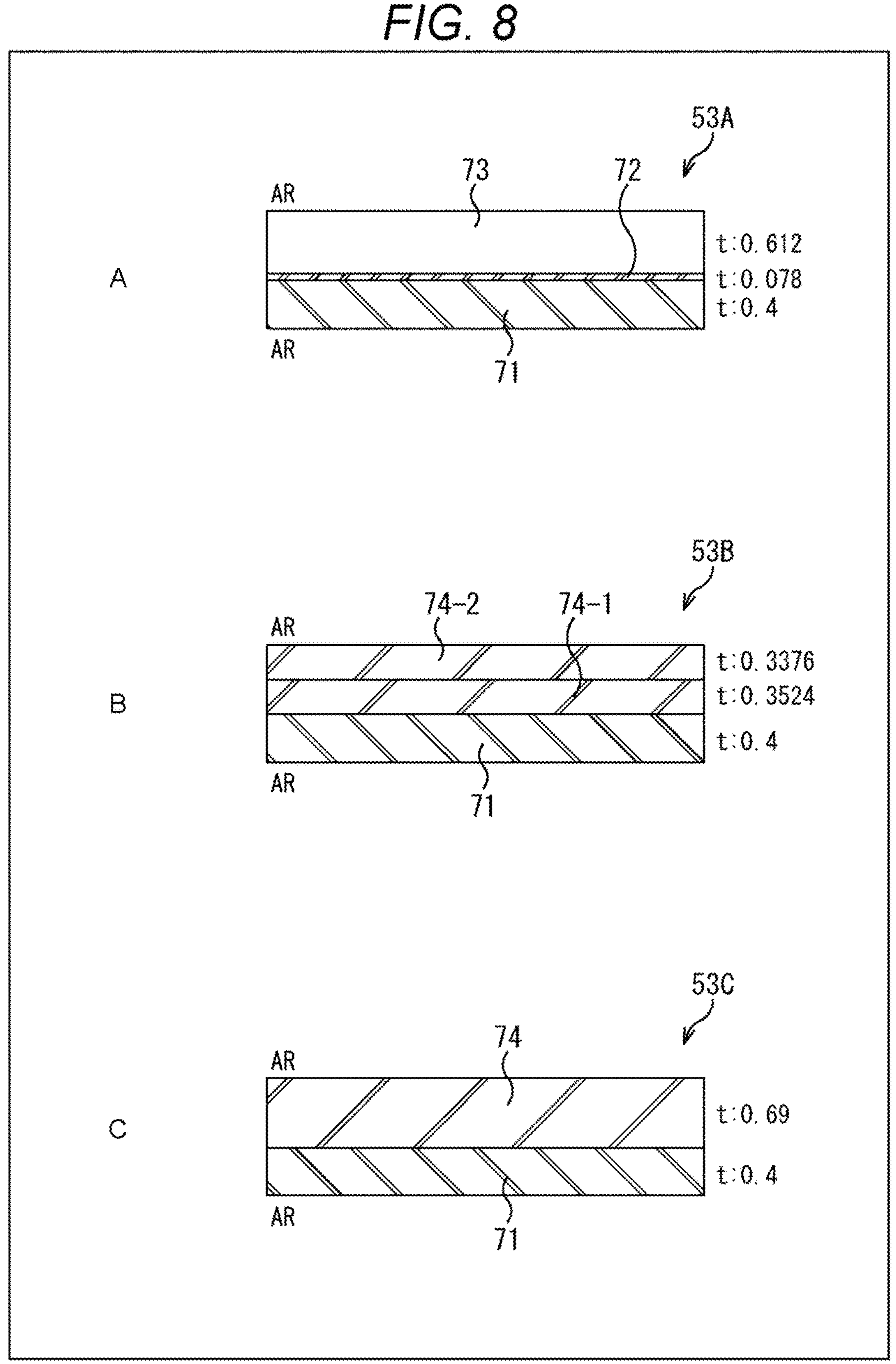
FIG. 8 is a diagram for explaining configuration examples of an optical element.
Figure 9:
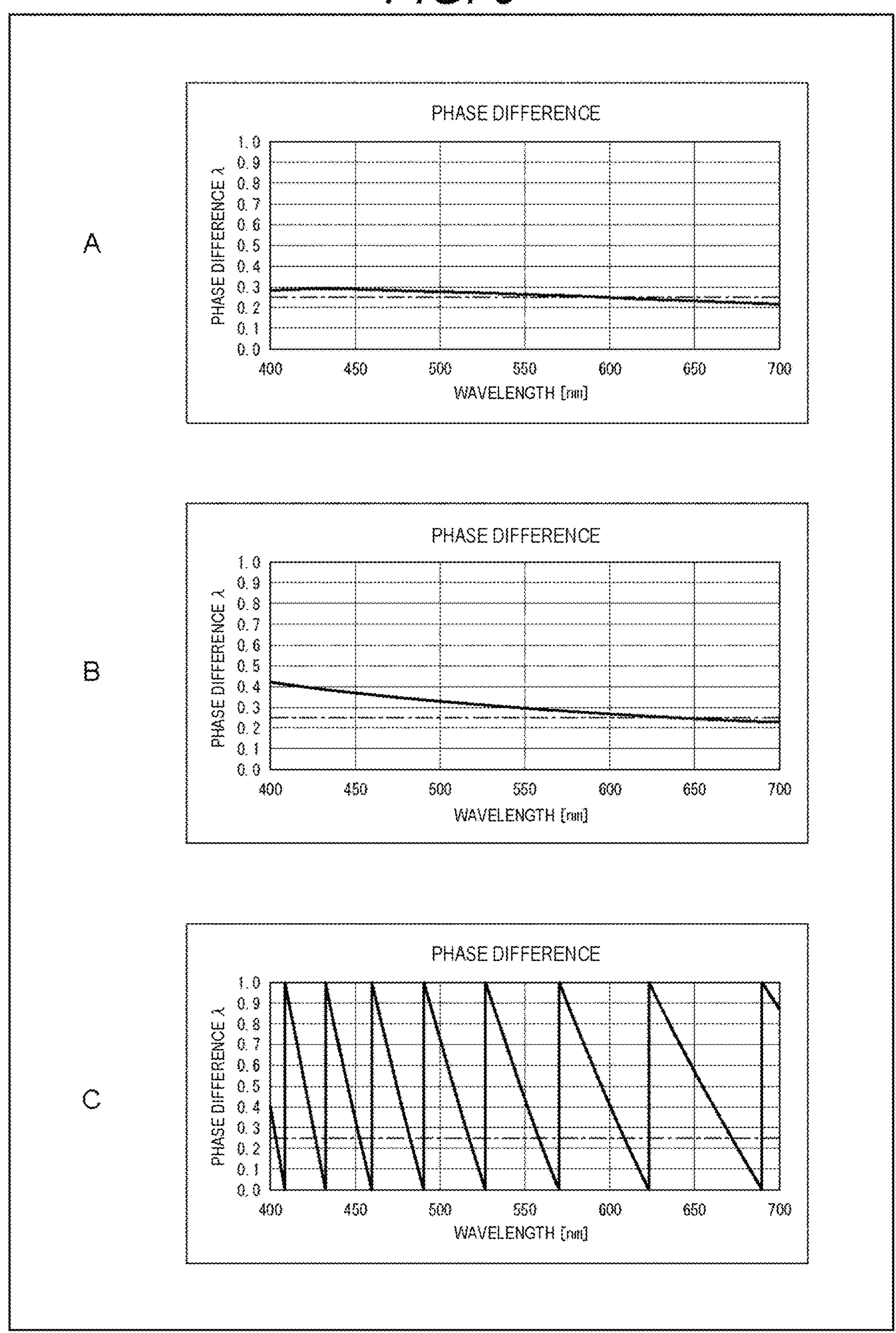
FIG. 9 is a diagram illustrating examples of phase difference characteristics of the optical elements.

FIG. 8 illustrates configuration examples of the optical elements 53A to 53C having a thickness of 1.09 mm, and FIG. 9 illustrates phase difference characteristics of the optical elements 53A to 53C.

A of FIG. 8 illustrates the optical element 53A having a laminated structure in which a color correction filter 71 having a thickness of 0.4 mm, a retardation film 72 having a thickness of 0.078 mm, and glass 73 having a thickness of 0.612 mm are laminated. As illustrated in A of FIG. 9, the optical element 53A having such a configuration substantially coincides with an ideal line (¼=0.25λ) represented by the alternate long and short dash line in all the wavelength regions, and has the phase difference characteristic that can reliably cancel polarization. For example, the optical element 53A is adopted when low cost is required.

B of FIG. 8 illustrates the optical element 53B having a laminated structure in which a color correction filter 71 having a thickness of 0.4 mm, a crystal plate 74-1 having a thickness of 0.3524 mm, and a crystal plate 74-2 having a thickness of 0.3376 mm are laminated. For example, the crystal plate 74-1 and the crystal plate 74-2 are laminated in a direction in which the crystal directions are orthogonal to each other. As illustrated in B of FIG. 9, the optical element 53B having such a configuration has a phase difference characteristic close to the ideal line (¼=0.25λ) represented by the alternate long and short dash line, and has the phase difference characteristic that can sufficiently cancel polarization. For example, the optical element 53B is adopted when used in a high-temperature and high-humidity environment. Note that the thickness error of each of the color correction filter 71 and the crystal plates 74-1 and 74-2 is preferably within ±10%. More preferably, the thickness error of each of the color correction filter 71 and the crystal plates 74-1 and 74-2 is preferably within ±5%. Yet more preferably, the thickness error of each of the color correction filter 71 and the crystal plates 74-1 and 74-2 is preferably within ±3%.

C of FIG. 8 illustrates the optical element 53C having a laminated structure in which a color correction filter 71 having a thickness of 0.4 mm and a crystal plate 74 having a thickness of 0.69 mm are laminated. As illustrated in C of FIG. 9, it is a matter of course that the optical element 53C having such a configuration has a phase difference characteristic that periodically becomes close to the ideal line (¼=0.25λ) represented by the alternate long and short dash line and enables polarization to be canceled depending on the wavelength, and if the cycle in which the phase difference returns to the original state is sufficiently short with respect to the bandwidth of the wavelength, the optical element 53C can eliminate the difference in p- and s-polarized light at a level at which there is no problem in practical use.

<Optical Configuration of Imaging Module>

An optical configuration of the imaging module 41 will be described with reference to FIGS. 10 to 13.

In the medical imaging system 11, the imaging module 41 has an optical configuration in which the imaging element 52-1 captures a Mid image, the imaging element 52-2 captures a Near image, and the imaging element 52-3 captures a Far image.

Figure 10:
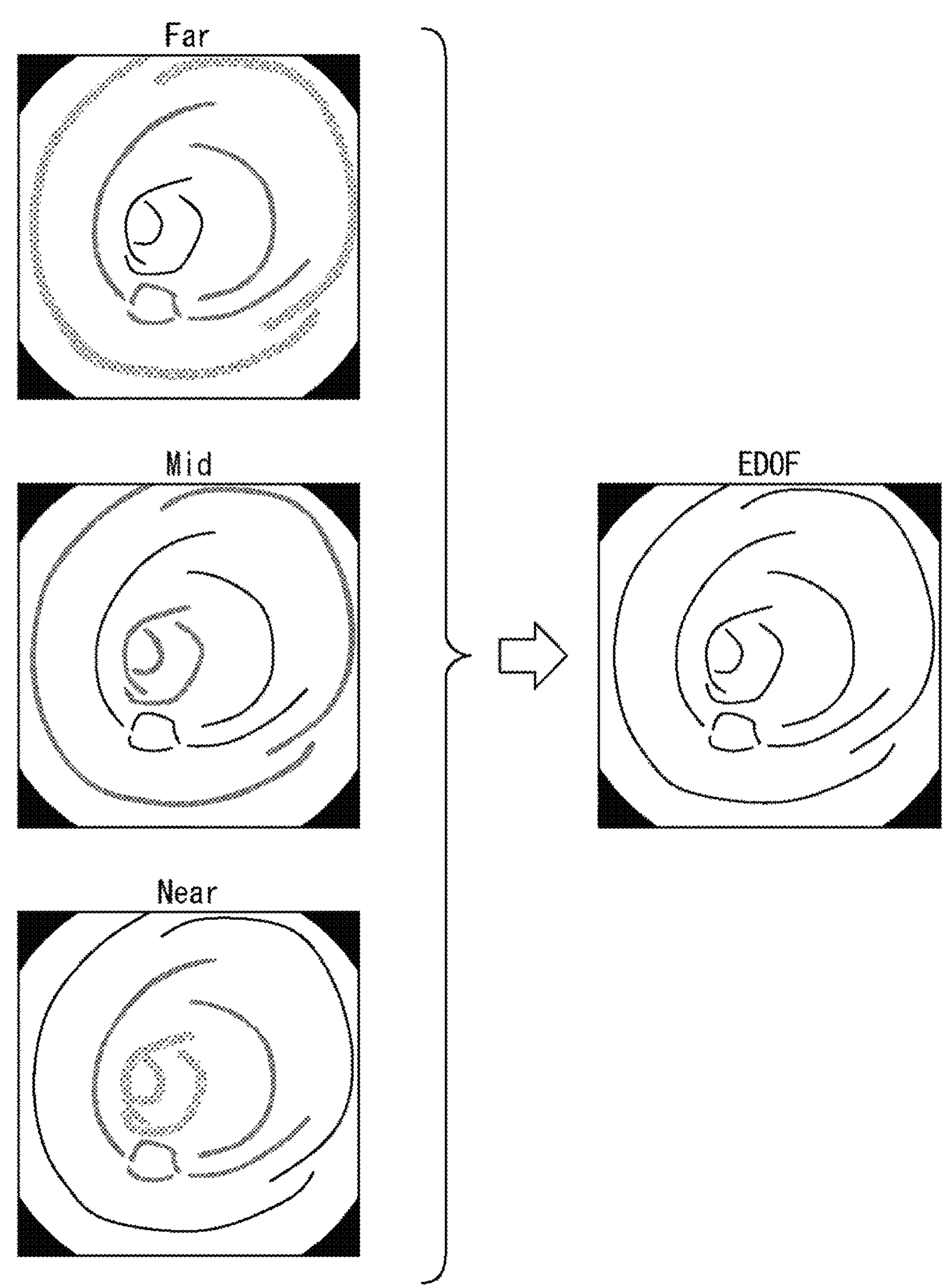
FIG. 10 is a view for explaining generation of an EDoF image.

As illustrated in FIG. 10, the Near image is an image captured so as to be focused on a near point, and blurring increases toward the far point side. The Mid image is an image captured so as to be focused on an intermediate point, and blurring occurs on the near point side and the far point side. The Far image is an image captured so as to be focused on the far point side, and blurring increases toward the near point side.

Then, in the medical imaging system 11, the CCU 32 compares image output signals of the Near image, the Mid image, and the Far image, selects regions with the highest contrast, and performs image processing of joining the selected regions. Therefore, it is possible to generate an EDoF image having a depth of field that is, for example, three times the depth of field of the CCU 32, the Near image, the Mid image, and the Far image. As described above, the CCU 32 can be implemented by relatively light-load image processing of only performing region selection processing and region joining processing.

Here, as described above, with the imaging element 52-1 as a reference position, the imaging element 52-2 is arranged at a position farther from the branching optical system 51 than the reference position by the shift amount ΔZ, and the imaging element 52-3 is arranged at a position closer to the branching optical system 51 than the reference position by the shift amount ΔZ.

An adjustment method of adjusting the arrangement of the imaging elements 52-1 to 52-3 on the basis of the shift amount ΔZ in this manner will be described.

First, the imaging elements 52-1 to 52-3 are arranged so as to have a prescribed flange focal length (in air) (for example, 17.526 mm in the case of using a C mount) with respect to the attachment reference surface of the imaging lens 42. At this point, object-image conjugate distances from the subject to the imaging elements 52-1 to 52-3 are the same.

Next, the imaging element 52-2 is moved away from the branching optical system 51 by the shift amount ΔZ, and the imaging element 52-3 is moved closer to the branching optical system 51 by the shift amount ΔZ. In this manner, the object-image conjugate distances of the imaging elements 52-2 and 52-3 are changed with respect to the object-image conjugate distance of the imaging element 52-1.

Therefore, the imaging module 41 can have an optical configuration in which the imaging element 52-1 focuses on a subject at an intermediate distance, the imaging element 52-2 focuses on a subject at a short distance, and the imaging element 52-3 focuses on a subject at a long distance.

Note that the imaging module 41 has a configuration in which each of the imaging elements 52-1 to 52-3 is separated from the branching optical system 51 with an air gap therebetween. Therefore, the imaging elements 52-1 to 52-3 can be fixed (for example, bonded) to the branching optical system 51 after 6-axis adjustment (x-axis direction, y-axis direction, z-axis direction, angle around x-axis, angle around y-axis, angle around z-axis) in the air. Therefore, the imaging module 41 can enable partial blur adjustment of the imaging lens 42, and for example, can capture an image with higher image quality than the endoscope system of Patent Document 1 described above.

Here, a calculation method for determining the optimum shift amount ΔZ on the basis of geometric optics will be described with reference to FIGS. 11 and 12.

For example, in a case where the shift amount ΔZ is too small, an EDoF image in which depth extension is not sufficiently performed is acquired, and in a case where the shift amount ΔZ is too large, an EDoF image in which local blur occurs and resolution is reduced is acquired. Therefore, it is necessary to determine the optimum shift amount ΔZ for capturing a high-quality image with a deep depth of field and high resolution.

For example, as illustrated in FIG. 11, in a case where the imaging element 52 is arranged at a position b' at a prescribed flange focal length from the principal point of the imaging lens 42, a subject at a position b is formed as an image on the sensor surface of the imaging element 52, and becomes a point image on the sensor surface of the imaging element 52.

At this time, the subject at a position a farther than the position b is formed as an image at a position a' on the front side of the position b'. Therefore, on the sensor surface of the imaging element 52, the subject at the position a is imaged with a blur width having the permissible circle of confusion δ as a diameter. In contrast, the subject at a position c closer than the position b is imaged at a position c' on the back side of the position b'. Therefore, on the sensor surface of the imaging element 52, the subject at the position c is imaged with a blur width having the permissible circle of confusion δ as a diameter. Note that, as an approximation in a case where the distance from the principal point of the imaging lens 42 to a subject is sufficiently long, the front depth of focus and the back depth of focus are equal. Furthermore, the depth of focus is an amount on the image side, and the depth of field is obtained by converting the amount on the object side.

Then, the depth of focus DoF is expressed as DoF=δ×F using the permissible circle of confusion δ and the aperture value F of the imaging lens 42, and the shift amount ΔZ of each of the imaging elements 52-2 and 52-3 with respect to the imaging element 52-1 is calculated as shift amount ΔZ=2×DoF=2×δ×F. That is, by determining the permissible circle of confusion δ and the aperture value F of the imaging lens 42, the optimum shift amount ΔZ of each of the imaging elements 52-2 and 52-3 can be determined.

Figure 12:
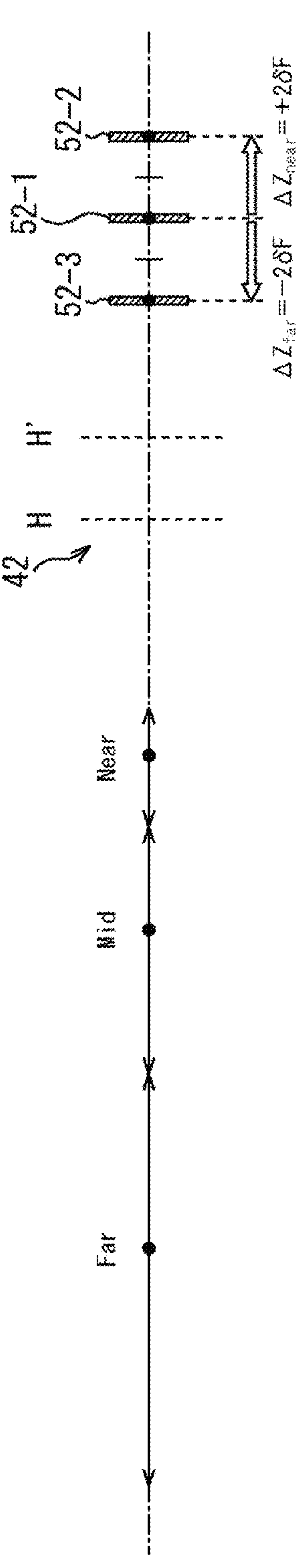
FIG. 12 is a diagram for explaining a range of a depth of field.

Therefore, as illustrated in FIG. 12, the range of the depth of field of the EDoF image can be set such that the depth of field of the Mid image captured by the imaging element 52-1, the depth of field of the Near image captured by the imaging element 52-2, and the depth of field of the Far image captured by the imaging element 52-3 are continuous. Therefore, the medical imaging system 11 can acquire a high-resolution EDoF image in which the depth of field can be made sufficiently deep and local blur caused by discontinuous depth of field is avoided.

Here, the permissible circle of confusion δ is the maximum diameter of blur that can be recognized as not being blurred by human eyes, and is a sensory physical quantity. Therefore, how to determine the permissible circle of confusion δ is important.

Figure 13:
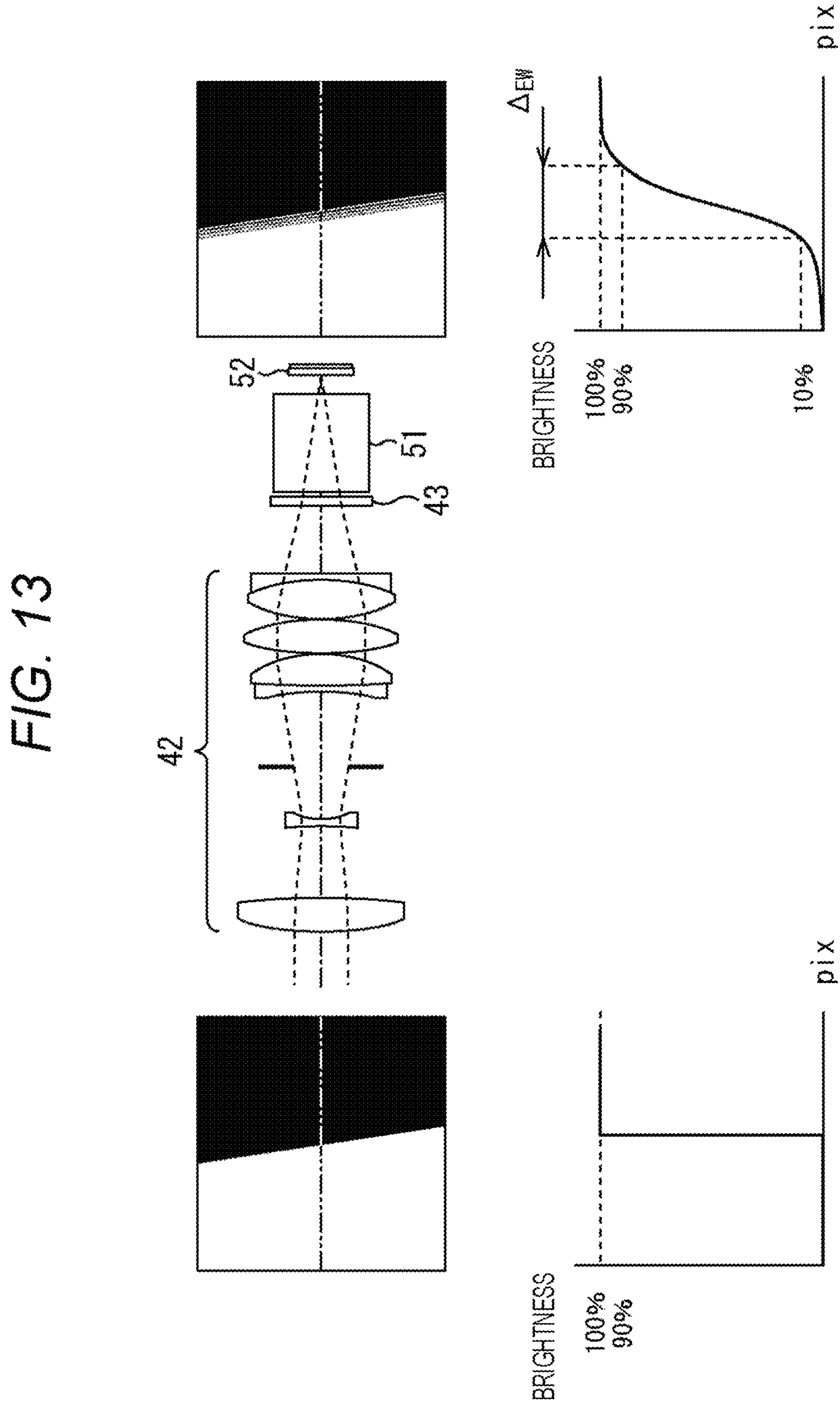
FIG. 13 is a diagram for explaining the definition of a permissible circle of confusion.

Therefore, in the present embodiment, as illustrated in FIG. 13, a blur width when a black-and-white edge object passes through the imaging lens 42 and forms an image on the sensor surface of imaging element 52, that is, an edge blur width $\Delta_{EW}$ between a position where the normalization intensity of a black-and-white edge image is 0.1 and a position where the normalization intensity is 0.9 is defined as a permissible circle of confusion δ. Note that the edge blur width $\Delta_{EW}$ is a value in units of pixels of the imaging element 52. Note that the black-and-white edge image may be expressed as an edge response function.

Therefore, in the category of geometric optics, the depth of focus DoF is calculated as DoF=$\Delta_{EW}$×p×F using the edge blur width $\Delta_{EW}$, the pixel pitch p of the imaging element 52, and the aperture value F of the imaging lens 42. As a result, the shift amount ΔZ becomes ΔZ=2×DoF=2×$\Delta_{EW}$×p×F.

Specifically, in a case where the pixel pitch p of the imaging element 52 is 1.26 μm and the aperture value F of the imaging lens 42 is 4, if an allowable blur width is defined as an edge blur width $\Delta_{EW}$ of up to five pixels, the shift amount ΔZ can be calculated as 50.4 μm (=2×5×1.26×4).

As described above, the optimum shift amount ΔZ can be determined in the category of geometric optics. Moreover, in practice, it is necessary to think in terms of wave optics. That is, in wave optics, even on the best focus plane where a point image is formed on the sensor surface of the imaging element 52 on the basis of geometric optics, the point image does not actually become an infinitesimal point due to the influence of diffraction, aberration, and the like, and has a certain degree of blur width.

Therefore, if the optimum shift amount ΔZ is determined by using the correction term M for wave-optically correcting the shift amount ΔZ, the shift amount ΔZ becomes ΔZ=2×DoF×M.

Here, the inventors of the present application have found that the shift amount ΔZ is optimal in terms of wave optics by setting the correction term M within the range of 1<M<2. The lower limit value of the correction term M is consistent with the geometric optical calculation method, and in a case where the correction term M is less than the lower limit value, sufficient depth extension cannot be achieved. In contrast, in a case where the correction term M exceeds the upper limit value of the correction term M, local blur occurs in the EDoF image.

Specifically, in a case where the pixel pitch p of the imaging element 52 is 1.26 μm and the aperture value F of the imaging lens 42 is 4, if an allowable blur width is defined as an edge blur width $\Delta_{EW}$ of up to five pixels, it is sufficient if the shift amount ΔZ satisfies 50.4 μm<ΔZ<100.8 μm since the correction term M is within the range of 1<M<2. More preferably, the correction term M is within a range of 1<M<1.5, and it is sufficient if the shift amount ΔZ satisfies 50.4 μm<ΔZ<75.3 μm.

Moreover, the shift amount ΔZ can be adjusted by an adjustment value Δz in consideration of an error Δz' due to manufacturing variation when the imaging module 41 is manufactured.

For example, the actual shift amount ΔZ is ΔZ=Δz_dsn−Δz' with respect to the design value Δz_dsn of the shift amount ΔZ. At this time, as the error Δz', error factors such as a flange focal length adjustment error, a tilt adjustment error converted in the depth direction, and a reliability test variation can be considered. In a case where the imaging elements 52-2 and 52-3 are fixed with the shift amount ΔZ in which these error factors are not considered, if these error factors are random, the shift amount ΔZ actually becomes ΔZ=Δz_dsn+Δz', and the imaging module 41 is manufactured in some cases. In this case, as a result of unintentionally increasing the shift amount ΔZ, there is a concern that local blur will occur in an EDoF image.

Therefore, in consideration of these error factors, it is preferable that the shift amount ΔZ satisfies ΔZ=Δz_dsn−Δz'. Specifically, assuming that various manufacturing errors have a flange focal length adjustment error of ±25 μm, a tilt adjustment error converted in the depth direction of ±10 μm, and a reliability test variation of ±5 μm as 30 values, the square root of the sum of squares is about 30=Δz'=+23 μm. Therefore, in a case where the design value Δz_dsn is 60 μm, the shift amount ΔZ is preferably 37 μm (=60−23).

<Second Configuration Example of Imaging Module>

Figure 14:
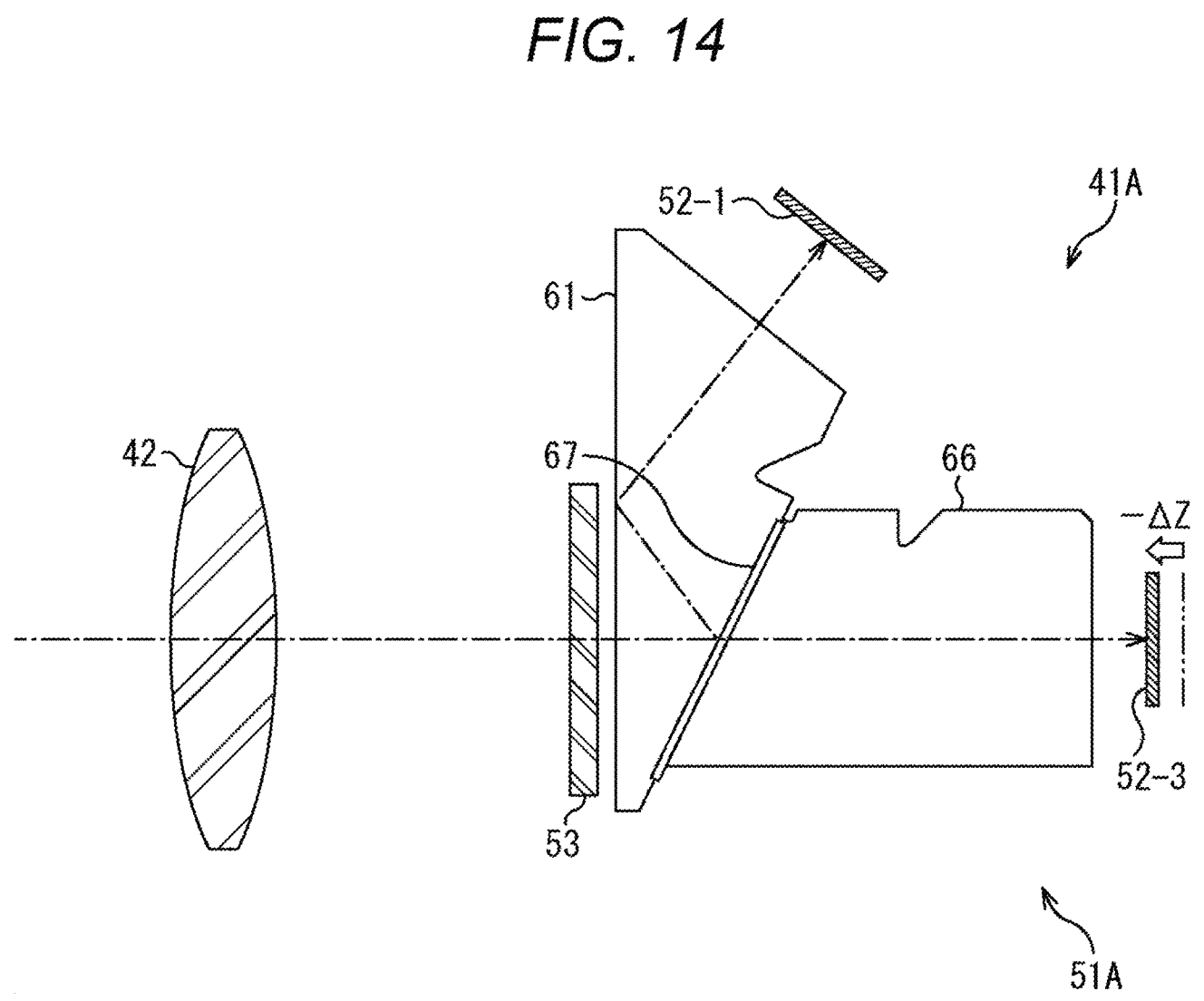

FIG. 14 is a view illustrating a second configuration example of the imaging module. In an imaging module 41A illustrated in FIG. 14, the same configurations as those of the imaging module 41 in FIG. 3 will be denoted by the same reference signs, and detailed description thereof will be omitted.

As illustrated in FIG. 14, the imaging module 41A includes a branching optical system 51A, two imaging elements 52-1 and 52-3, and an optical element 53. Furthermore, an imaging lens 42 is arranged on an optical axis of light incident on the imaging module 41A. That is, the imaging module 41A is configured such that light is branched in two directions toward the two imaging elements 52-1 and 52-3 by the branching optical system 51A.

Figure 15:
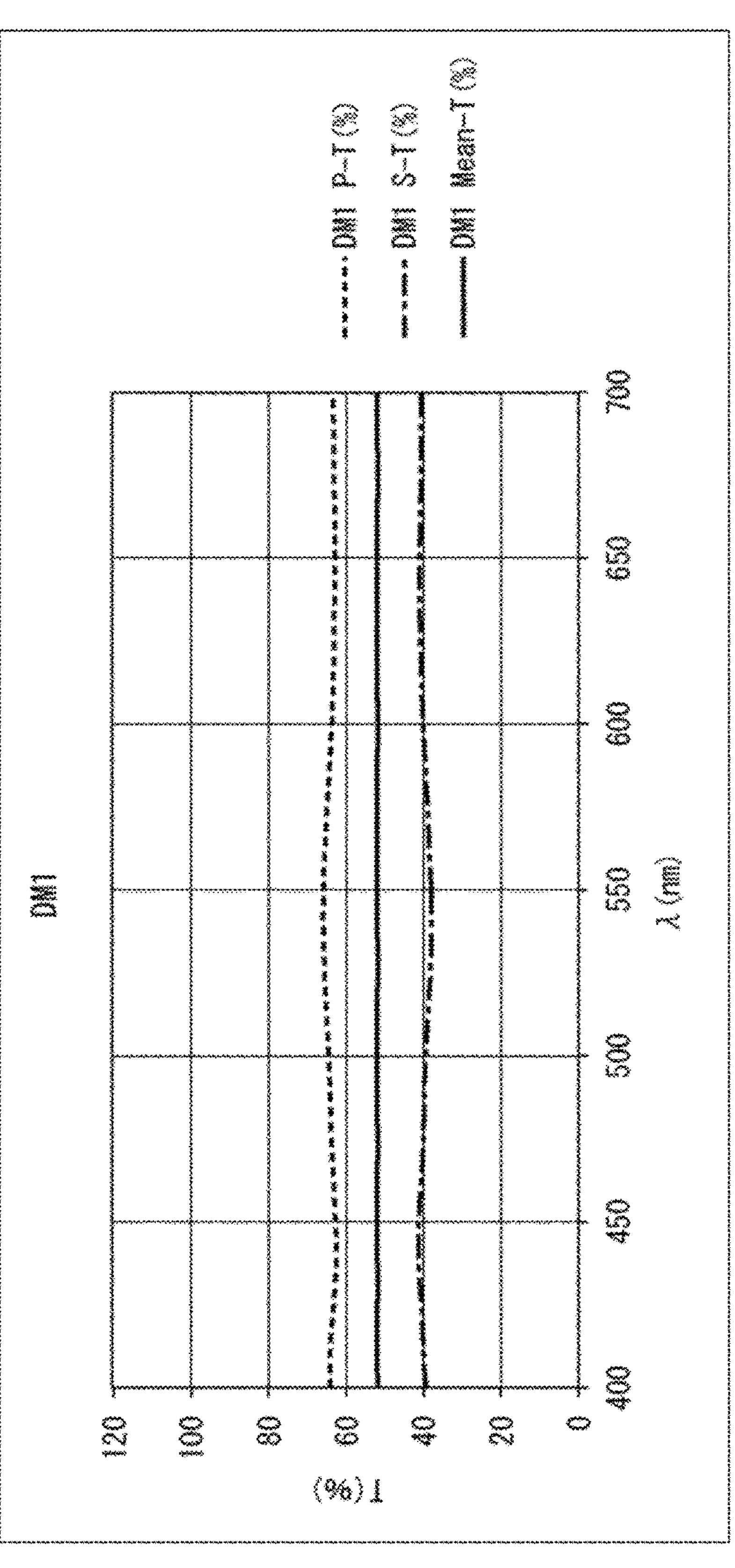
FIG. 15 is a diagram illustrating an example of characteristics of a dichroic mirror.

The branching optical system 51A includes a first prism 61, a second prism 66, and a dichroic mirror 67, and constitutes a prism block joined so as not to generate an air gap between the first prism 61 and the second prism 66. The dichroic mirror 67 is an optical thin film including a dielectric multilayer film formed on the emission surface of the first prism 61 on the second prism 66 side, and for example, branches light at a light amount at which average reflectance:average transmittance=1:1, as illustrated in FIG. 15. Furthermore, the dichroic mirror 67 branches light in a specific wavelength band including a visible light band from 400 nm to 700 nm, for example.

The imaging element 52-1 is arranged at a position where the optical distance from the principal point of the imaging lens 42 is a reference. The imaging element 52-3 is arranged at a position closer to the branching optical system 51 by the shift amount ΔZ such that the optical distance from the principal point of the imaging lens 42 is shorter than the reference.

The imaging module 41A configured as described above can capture a Mid image by the imaging element 52-1 and a Far image by the imaging element 52-3. Therefore, in a medical imaging system 11 including the imaging module 41A, an EDoF image can be generated by using the Mid image and the Far image and the EDoF image can be output to a display device 14. It is needless to say that the focal length of the imaging lens 42 may be adjusted such that the imaging element 52-1 captures a Near image and the imaging element 52-3 captures a Mid image.

An example of the medical imaging system to which the technology according to the present disclosure (present technology) can be applied has been described above. Note that the present technology is not limited to the above-described embodiments, usage examples and application examples, and various modifications can be made without departing from the scope of the present technology. For example, the imaging module and the image processing unit that performs EDoF image processing can be applied to an imaging system, and for example, can be applied to an imaging system for a broadcasting station, an in-vehicle imaging system, or the like.

Furthermore, effects described in the present description are merely examples and are not limited, and there may be other effects.

Examples of Configuration Combinations

Note that the present technology can also have the following configuration.

(1)

A medical imaging system including:

an imaging module provided in a medical imaging device, the imaging module including a branching optical system that branches light incident via an imaging lens in at least two directions and emits the light, and two or more imaging elements that receive the light emitted from the branching optical system in the at least two directions, respectively, and perform imaging; and an image processing unit that performs image processing of generating an extended depth of field (EDoF) image with an extended depth of field by using images captured by the two or more imaging elements, the two or more imaging elements being arranged at positions having different optical distances from a principal point of the imaging lens by a shift amount ΔZ, and the shift amount ΔZ being calculated from ΔZ=2×DoF×M (1<M<2) by using a depth of focus DoF of the imaging lens set on the basis of a pixel pitch p of the two or more imaging elements and an aperture value F of the imaging lens, and a correction term M.

(2)

The medical imaging system according to (1), in which the depth of focus DoF is calculated as $$\mathrm{DoF}=\Delta_{EW}\times p\times F$$

by using an edge blur width $\Delta_{EW}$ of a black-and-white edge image, the pixel pitch p of the two or more imaging elements, and the aperture value F of the imaging lens.

(3)

The medical imaging system according to (1), in which the correction term M is determined on the basis of wave optics.

(4)

The medical imaging system according to (1), in which the correction term M satisfies $1<M<1.5$.

(5)

The medical imaging system according to any one of (1) to (4), in which the branching optical system branches light incident via the imaging lens in three directions and emits the light, and as the two or more imaging elements, a first imaging element arranged at a reference position with respect to the branching optical system, a second imaging element arranged at a position farther from the branching optical system than the reference position by the shift amount ΔZ, and a third imaging element arranged at a position closer to the branching optical system than the reference position by the shift amount ΔZ are provided.

(6)

The medical imaging system according to (5), in which the branching optical system includes a prism block in which a first prism that emits light to the first imaging element, a second prism that emits light to the second imaging element, and a third prism that emits light to the third imaging element are joined in a gapless structure, a first optical thin film that branches light in a specific wavelength band with a light amount at which a ratio of average reflectance to average transmittance is 1:2 is provided between the first prism and the second prism, and a second optical thin film that branches light in a specific wavelength band at a light amount at which a ratio of average reflectance to average transmittance is 1:1 is provided between the second prism and the third prism.

(7)

The medical imaging system according to (6), in which the specific wavelength band includes a visible light band from 400 nm to 700 nm.

(8)

The medical imaging system according to any one of (1) to (4), in which the branching optical system branches light incident via the imaging lens in two directions and emits the light, and as the two or more imaging elements, a first imaging element arranged at a reference position with respect to the branching optical system, and a second imaging element arranged at a position farther from or closer to the branching optical system than the reference position by the shift amount ΔZ are provided.

(9)

The medical imaging system according to (8), in which the branching optical system includes a prism block in which a first prism that emits light to the first imaging element and a second prism that emits light to the second imaging element are joined in a gapless structure, and an optical thin film that branches light in a specific wavelength band at a light amount at which a ratio of average reflectance to average transmittance is 1:1 is provided between the first prism and the second prism.

(10)

The medical imaging system according to (9), in which the specific wavelength band includes a visible light band from 400 nm to 700 nm.

(11)

The medical imaging system according to any one of (1) to (10) further including an optical element that depolarizes light incident on the branching optical system.

(12)

An imaging device including:

an imaging module including a branching optical system that branches light incident via an imaging lens in at least two directions and emits the light, and two or more imaging elements that receive the light emitted from the branching optical system in the at least two directions, respectively, and perform imaging, the two or more imaging elements being arranged at positions having different optical distances from a principal point of the imaging lens by a shift amount ΔZ, and the shift amount ΔZ being calculated from $\Delta Z=2\times\mathrm{DoF}\times M$ $(1<M<2)$ by using a depth of focus DoF of the imaging lens set on the basis of a pixel pitch p of the two or more imaging elements and an aperture value F of the imaging lens, and a correction term M.

Note that the present embodiment is not limited to the above-described embodiment, and various modifications can be made without departing from the gist of the present disclosure. Furthermore, the effects described herein are merely examples and are not limited, and other effects may be provided.

REFERENCE SIGNS LIST

11 Medical imaging system
12 Endoscope
13 Energy treatment tool
14 Display device
15 Device unit
16 Forceps
21 Camera head
22 Lens barrel unit
31 Light source device
32 CCU
33 Recording device
34 Output device
41 Imaging module
42 Imaging lens
51 Branching optical system
52-1 to 52-3 Imaging element
53 Optical element
61 First prism
62 Second prism
63 Third prism
64 First dichroic mirror
65 Second dichroic mirror

The invention claimed is:

1. A medical imaging system comprising:

an imaging module provided in a medical imaging device, the imaging module including a branching optical system that branches light incident via an imaging lens in at least two directions and emits the light, and two or more light receiving regions of an image sensor configured to receive the light emitted from the branching optical system in the at least two directions, respectively, and perform imaging; and an image processing circuitry configured to perform image processing of generating an extended depth of field (EDoF) image with an extended depth of field by using images captured by the two or more light receiving elements, the two or more light receiving regions being arranged at positions having different optical distances from a principal point of the imaging lens by a shift amount $\Delta Z$, and the shift amount $\Delta Z$ being calculated as $\Delta Z=2\times DoF\times M$ $(1<M<2)$ by using a depth of focus DoF of the imaging lens set on a basis of a pixel pitch p of the two or more light receiving regions and an aperture value F of the imaging lens, and a correction term M.

2. The medical imaging system according to claim 1, wherein the depth of focus DoF is calculated as $$DoF=\Delta_{EW}\times P\times F$$

by using an edge blur width $\Delta_{EW}$ of a black-and-white edge image, the pixel pitch p of the two or more light receiving regions and the aperture value F of the imaging lens.

3. The medical imaging system according to claim 1, wherein the correction term M is determined on a basis of wave optics.

4. The medical imaging system according to claim 1, wherein the correction term M satisfies $1<M<1.5$.

5. The medical imaging system according to claim 1, wherein the branching optical system branches light incident via the imaging lens in three directions and emits the light, and as the two or more light receiving regions, a first light receiving region arranged at a reference position with respect to the branching optical system, a second light receiving region arranged at a position farther from the branching optical system than the reference position by the shift amount $\Delta Z$, and a third light receiving region arranged at a position closer to the branching optical system than the reference position by the shift amount $\Delta Z$ are provided.

6. The medical imaging system according to claim 5, wherein the branching optical system includes a prism block in which a first prism that emits light to the first light receiving region, a second prism that emits light to the second light receiving region, and a third prism that emits light to the third light receiving region are joined in a gapless structure, a first optical thin film that branches light in a specific wavelength band with a light amount at which a ratio of average reflectance to average transmittance is 1:2 is provided between the first prism and the second prism, and a second optical thin film that branches light in a specific wavelength band at a light amount at which a ratio of average reflectance to average transmittance is 1:1 is provided between the second prism and the third prism.

7. The medical imaging system according to claim 6, wherein the specific wavelength band includes a visible light band from 400 nm to 700 nm.

8. The medical imaging system according to claim 1, wherein the branching optical system branches light incident via the imaging lens in two directions and emits the light, and as the two or more light receiving regions, a first light receiving region arranged at a reference position with respect to the branching optical system, and a second light receiving region arranged at a position farther from or closer to the branching optical system than the reference position by the shift amount $\Delta Z$ are provided.

9. The medical imaging system according to claim 8, wherein the branching optical system includes a prism block in which a first prism that emits light to the first light receiving region and a second prism that emits light to the second light receiving region are joined in a gapless structure, and an optical thin film that branches light in a specific wavelength band at a light amount at which a ratio of average reflectance to average transmittance is 1:1 is provided between the first prism and the second prism.

10. The medical imaging system according to claim 9, wherein the specific wavelength band includes a visible light band from 400 nm to 700 nm.

11. The medical imaging system according to claim 1 further comprising an optical element that depolarizes light incident on the branching optical system.

12. An imaging device comprising:

an imaging module including a branching optical system that branches light incident via an imaging lens in at least two directions and emits the light, and two or more light receiving regions that receive the light emitted from the branching optical system in the at least two directions, respectively, and perform imaging, the two or more light receiving regions being arranged at positions having different optical distances from a principal point of the imaging lens by a shift amount $\Delta Z$, and the shift amount $\Delta Z$ being calculated as $\Delta Z=2\times DoF\times M$ $(1<M<2)$ by using a depth of focus DoF of the imaging lens set on a basis of a pixel pitch p of the two or more light receiving regions and an aperture value F of the imaging lens, and a correction term M.

* * * * *